US00PP23272P2

(12) United States Plant Patent
Nakano

(10) Patent No.: US PP23,272 P2
(45) Date of Patent: Dec. 25, 2012

(54) ***BOUGAINVILLEA* PLANT NAMED 'KOIRO'**

(50) Latin Name: *Bougainvillea×hybrida*
Varietal Denomination: Koiro

(75) Inventor: Masahiro Nakano, Aichi (JP)

(73) Assignee: Suntory Flowers Ltd., Tokyo (JP)

( * ) Notice: Subject to any disclaimer, the term of this patent is extended or adjusted under 35 U.S.C. 154(b) by 35 days.

(21) Appl. No.: 13/066,059

(22) Filed: Apr. 5, 2011

(51) Int. Cl.
*A01H 5/00* (2006.01)

(52) U.S. Cl. ..... Plt./256

(58) Field of Classification Search ..... Plt./256
See application file for complete search history.

*Primary Examiner* — Susan McCormick Ewoldt
(74) *Attorney, Agent, or Firm* — C. A. Whealy

(57) ABSTRACT

A new and distinct cultivar of *Bougainvillea* plant named 'Koiro', characterized by its compact, upright and mounding plant habit; moderately vigorous growth habit; relatively small leaves; freely flowering habit; vivid red purple-colored flower bracts; and good garden performance.

1 Drawing Sheet

Botanical designation: *Bougainvillea×hybrida.*
Cultivar denomination: 'KOIRO'.

BACKGROUND OF THE INVENTION

The present invention relates to a new and distinct cultivar of *Bougainvillea* plant, botanically known as *Bougainvillea× hybrida* and hereinafter referred to by the name 'Koiro'.

The new *Bougainvillea* plant is a naturally-occurring branch mutation of the proprietary cultivar *Bougainvillea× hybrida* 'Konatu', not patented. The new *Bougainvillea* plant was discovered and selected by the Inventor on a single flowering plant within a population of plants of 'Konatu' in a controlled greenhouse environment in Tsushima-shi, Aichi, Japan in April, 2006.

Asexual reproduction of the new *Bougainvillea* plant by cuttings in a controlled greenhouse environment in Tsushima-shi, Aichi, Japan since May, 2006, has shown that the unique features of this new *Bougainvillea* plant are stable and reproduced true to type in successive generations.

SUMMARY OF THE INVENTION

Plants of the new *Bougainvillea* have not been observed under all possible environmental conditions and cultural practices. The phenotype may vary somewhat with variations in environment such as temperature and light intensity without, however, any variance in genotype.

The following traits have been repeatedly observed and are determined to be the unique characteristics of 'Koiro'. These characteristics in combination distinguish 'Koiro' as a new and distinct *Bougainvillea* plant:

1. Compact, upright and mounding plant habit.
2. Moderately vigorous growth habit.
3. Relatively small leaves.
4. Freely flowering habit.
5. Vivid red purple-colored flower bracts.
6. Good garden performance.

Plants of the new *Bougainvillea* differ from plants of the parent, 'Konatu', primarily in flower bract color as plants of 'Konatu' have less vivid and lighter red purple-colored flowers than plants of the new *Bougainvillea.*

Plants of the new *Bougainvillea* can also be compared to plants of *Bougainvillea×buttiana* 'Mrs. Butt', not patented. In side-by-side comparisons conducted in Tsushima-shi, Aichi, Japan, plants of the new *Bougainvillea* and 'Mrs. Butt' differed in the following characteristics:

1. Plants of the new *Bougainvillea* were much more compact than and not as vigorous as plants of 'Mrs. Butt'.
2. Plants of the new *Bougainvillea* were more upright than and not as outwardly spreading and trailing as plants of 'Mrs. Butt'.
3. Plants of the new *Bougainvillea* were more freely branching than plants of 'Mrs. Butt'.
4. Plants of the new *Bougainville* had much shorter internodes than plants of 'Mrs. Butt'.
5. Plants of the new *Bougainvillea* were spineless whereas plants of 'Mrs. Butt' had spines.
6. Plants of the new *Bougainvillea* had smaller leaves than plants of 'Mrs. Butt'.
7. Plants of the new *Bougainvillea* had smaller inflorescences than plants of 'Mrs. Butt'.
8. Plants of the new *Bougainvillea* and 'Mrs. Butt' differed in flower bract color as plants of 'Mrs. Butt' had lighter red purple-colored flower bracts.
9. Plants of the new *Bougainvillea* had much shorter peduncles and pedicels than plants of 'Mrs. Butt'.

BRIEF DESCRIPTION OF THE PHOTOGRAPHS

The accompanying colored photographs illustrate the overall appearance of the new *Bougainvillea* plant showing the colors as true as it is reasonably possible to obtain in colored reproductions of this type. Colors in the photographs may differ slightly from the color values cited in the detailed botanical description which accurately describe the colors of the new *Bougainvillea* plant.

The photograph at the top of the sheet comprises a side perspective view of a typical flowering plant of 'Koiro' grown in a container.

The photograph at the bottom of the sheet is a close-up view of a typical flowering plant of 'Koiro'.

DETAILED BOTANICAL DESCRIPTION

The aforementioned photographs and following observations, measurements and values describe plants grown during the autumn and early winter in 12-cm containers in a polyethylene-covered greenhouse in Tsushima, Aichi, Japan and under commercial cultural practices. During the production of the plants, day temperatures ranged from 10° C. to 30° C. and night temperatures averaged 13° C. Plants were six months old when the description and photographs were taken. In the following description, color references are made to The Royal Horticultural Society Colour Chart, 2007 Edition, except where general terms of ordinary dictionary significance are used.

Botanical classification: *Bougainvillea×hybrida* 'Koiro'.

Parentage: Naturally-occurring branch mutation of the proprietary cultivar *Bougainvillea×hybrida* 'Konatu', not patented.

Propagation:

*Type*.—By cuttings.

*Time to produce a rooted young plant, summer*.—About 22 days at 20° C. to 30° C.

*Time to produce a rooted young plant, winter*.—About 30 days at 20° C. to 25° C.

*Root description*.—Fibrous; white in color.

*Rooting habit*.—Freely branching habit; medium in density.

Plant description:

*Plant form and growth habit*.—Compact, upright and mounding plant habit; moderately vigorous growth habit; freely branching habit, pinching enhances branching potential.

*Plant height*.—About 16.2 cm.

*Plant width*.—About 17 cm.

*Lateral branches*.—Length: About 8.2 cm. Diameter: About 2.1 mm. Internode length: About 2.3 cm. Strength: Strong. Texture: Smooth, glabrous; spineless. Color: Close to N144A; with development, close to 199A.

Foliage description:

*Arrangement*.—Alternate, simple.

*Length*.—About 3.6 cm.

*Width*.—About 2.1 cm.

*Shape*.—Ovate.

*Apex*.—Acute.

*Base*.—Obtuse.

*Margin*.—Entire.

*Texture, upper and lower surfaces*.—Pubescent.

*Venation pattern*.—Pinnate, reticulate.

*Color*.—Developing leaves, upper surface: Close to 144B. Developing leaves, lower surface: Close to 146C. Fully expanded leaves, upper surface: Close to 144A; venation, close to 145C. Fully expanded leaves, lower surface: Close to 144B; venation, close to 145C.

*Petioles*.—Length: About 1.1 cm. Diameter: About 1 mm. Texture, upper and lower surfaces: Smooth, glabrous. Color, upper and lower surfaces: Close to 199B.

Flower description:

*Flower type and habit*.—Single flowers arranged in axillary clusters with showy flower bracts; freely flowering habit with about two to three flowers per cluster and about nine clusters developing per plant; flowers face mostly upright.

*Fragrance*.—None detected.

*Natural flowering season*.—Plants of the new *Bougainvillea* begin flowering about 30 days after planting; plants flower from late spring through the autumn in Japan.

*Flower longevity*.—Flowers last about 15 days on the plant; flowers not persistent; flower bracts persistent.

*Inflorescence diameter*.—About 3 cm.

*Inflorescence height*.—About 2.2 cm.

*Flower diameter*.—About 6.7 mm.

*Flower depth* (*height*).—About 1.6 cm.

*Flower buds*.—Length: About 1.5 cm. Diameter: About 1.9 mm. Shape: Elongated. Color: Close to 60B to 60C.

*Perianth*.—Arrangement: Five segments fused into a perianth tube with a shallow five-lobed perianth limb. Perianth limb: Length: About 2.2 mm. Diameter: About 2 mm. Shape: Lanceolate. Apex: Acute. Margin: Entire. Texture: Smooth, glabrous. Color: When opening, upper and lower surfaces: Close to 5D. Fully opened, upper and lower surfaces: Close to 155A. Perianth tube: Length: About 1.2 cm. Diameter: About 2.1 mm. Texture: Smooth, glabrous. Color, inner and outer surfaces: Close to 59A.

*Flower bracts*.—Quantity per flower: One. Length: About 2.1 cm. Width: About 1.4 cm. Shape: Ovate. Apex: Acute. Base: Obtuse. Margin: Entire; slightly undulate. Texture, upper and lower surfaces: Smooth; glabrous. Color: When opening, upper and lower surfaces: Close to 72A; venation, close to N79B. Fully opened, upper and lower surfaces: Close to 72A; venation, close to N79B.

*Peduncles*.—Length: About 3.6 mm. Diameter: About 1 mm. Texture: Smooth, glabrous. Angle: Outwardly. Color: Close to 166A tinted with close to 60C.

*Pedicels*.—Length: About 4.4 mm. Diameter: About 0.8 mm. Texture: Smooth, glabrous. Angle: Outwardly. Color: Close to 183B and 185B.

*Reproductive organs*.—Androecium: Stamens per flower: About eight. Stamen length: About 1 cm. Anther shape: Oval. Anther size: About 0.5 mm by 0.5 mm. Anther color: Close to 11A. Pollen amount: Scarce. Pollen color: Close to 11A. Gynoecium: Quantity of pistils per flower: One. Pistil length: About 1 cm. Stigma shape: Lanceolate. Stigma color: Close to 145C. Style color: Close to 145C. Ovary color: Close to 145B.

*Seed/fruit*.—Seed and fruit development have not been observed.

Disease/pest resistance: Plants of the *Bougainvillea* have not been observed to be resistant to pathogens and pests common to *Bougainvillea*.

Garden performance: Plants of the new *Bougainvillea* have been observed to have good garden performance and to tolerate rain, wind and temperatures ranging from about 5° C. to about 40° C.

It is claimed:

1. A new and distinct *Bougainvillea* plant named 'Koiro' as illustrated and described.

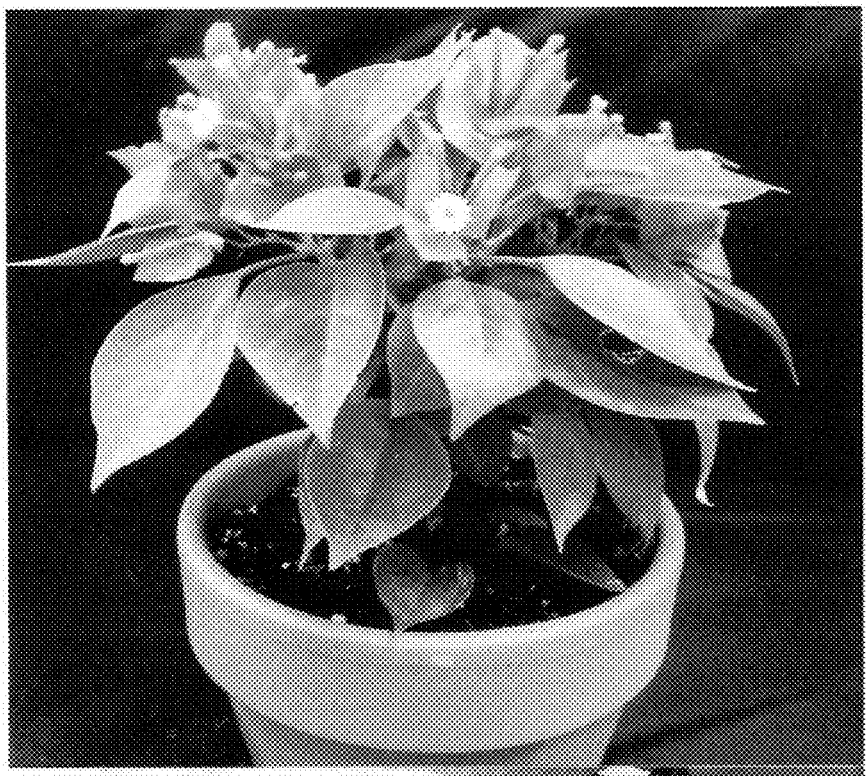
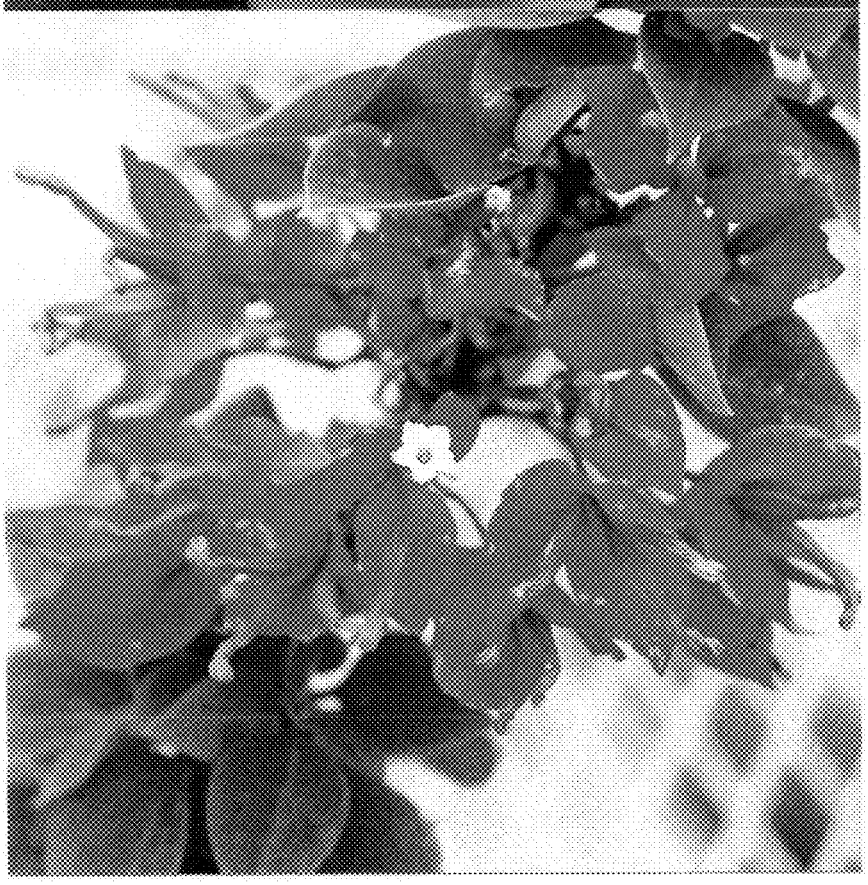

* * * * *